US011534390B2

(12) United States Patent
Pujol et al.

(10) Patent No.: US 11,534,390 B2
(45) Date of Patent: Dec. 27, 2022

(54) DISPERSIONS COMPRISING AT LEAST ONE NON-VOLATILE HYDROCARBON OIL

(71) Applicant: CAPSUM, Marseilles (FR)

(72) Inventors: Amélie Pujol, Marseilles (FR); Hélène Balbusquier, Sainte-Radegonde (FR); Mathieu Goutayer, Saint Malo (FR)

(73) Assignee: CAPSUM, Marseilles (FR)

( * ) Notice: Subject to any disclaimer, the term of this patent is extended or adjusted under 35 U.S.C. 154(b) by 0 days.

(21) Appl. No.: 16/626,820

(22) PCT Filed: Jun. 26, 2018

(86) PCT No.: PCT/EP2018/067140
§ 371 (c)(1),
(2) Date: Dec. 26, 2019

(87) PCT Pub. No.: WO2019/002308
PCT Pub. Date: Jan. 3, 2019

(65) Prior Publication Data
US 2020/0129413 A1 Apr. 30, 2020

(30) Foreign Application Priority Data

Jun. 27, 2017 (FR) .................................... 17 55907

(51) Int. Cl.
A61K 8/92 (2006.01)
A61K 8/81 (2006.01)
A61K 8/898 (2006.01)
A61K 8/04 (2006.01)
A61K 8/11 (2006.01)
A61K 8/73 (2006.01)
A61K 8/06 (2006.01)
A61Q 5/00 (2006.01)
A61Q 19/00 (2006.01)
A61Q 5/12 (2006.01)

(52) U.S. Cl.
CPC .............. *A61K 8/898* (2013.01); *A61K 8/042* (2013.01); *A61K 8/922* (2013.01); *A61Q 5/12* (2013.01)

(58) Field of Classification Search
None
See application file for complete search history.

(56) References Cited

U.S. PATENT DOCUMENTS

| 5,783,657 | A | 7/1998 | Pavlin et al. |
| 5,874,069 | A | 2/1999 | Mendolia et al. |
| 5,885,561 | A | 3/1999 | Flemming et al. |
| 5,891,450 | A | 4/1999 | Miyajima et al. |
| 5,919,441 | A | 7/1999 | Mendolia et al. |
| 5,981,680 | A | 11/1999 | Petroff et al. |
| 6,051,216 | A | 4/2000 | Barr et al. |
| 6,843,982 | B1 * | 1/2005 | Arnaud ................... A61P 17/00 424/64 |
| 9,993,398 | B2 | 6/2018 | Goutayer et al. |
| 10,300,006 | B2 | 5/2019 | Goutayer et al. |
| 2014/0045949 | A1 * | 2/2014 | Goutayer ................. A23D 7/02 514/772.6 |
| 2019/0060186 | A1 | 2/2019 | Goutayer et al. |

FOREIGN PATENT DOCUMENTS

| EP | 1386600 A1 * | 2/2004 | ............... A61Q 1/06 |
| FR | 2660212 A1 | 10/1991 | |
| FR | 2972367 A1 | 12/2012 | |
| FR | 2976824 A1 | 12/2012 | |
| FR | 2999921 A1 | 6/2014 | |
| FR | 3041251 A1 | 3/2017 | |
| WO | 9805294 A1 | 2/1998 | |
| WO | WO-9805294 A1 * | 2/1998 | ............. A61K 8/463 |
| WO | 0247619 A2 | 6/2002 | |
| WO | 02056847 A1 | 7/2002 | |
| WO | 2009069933 A2 | 6/2009 | |
| WO | 2009069933 A3 | 6/2009 | |
| WO | 2012120043 A2 | 9/2012 | |
| WO | 2015055748 A1 | 4/2015 | |
| WO | 2017046305 A1 | 3/2017 | |

OTHER PUBLICATIONS

Elementis, "A Comparison of Meadowfoam Seed Oil and Jojoba Oil," 2011, pp. 1-21. (Year: 2011).*
Search Report for International Patent Application No. PCT/EP2018/067140 dated Mar. 29, 2018.
Search Report for French Application No. 17 55907 dated Mar. 29, 2018.
Induchem Switzerland; "Unispheres" TDS Unispheres, Verson 16, Sep. 22, 2009, pp. 1-10.

* cited by examiner

*Primary Examiner* — Brian Gulledge

(74) *Attorney, Agent, or Firm* — Pearne & Gordon LLP

(57) ABSTRACT

A dispersion containing a dispersed phase comprising drops and a continuous aqueous phase, preferably in the form of gel, in which the drops comprise a fatty phase containing at least one gelling agent, and in which the fatty phase comprises at least one non-volatile hydrocarbon oil H1 containing more than 90%, and preferably more than 95%, fatty acids having at least 18 carbon atoms and preferably at least 20 carbon atoms.

21 Claims, No Drawings

DISPERSIONS COMPRISING AT LEAST ONE NON-VOLATILE HYDROCARBON OIL

This is a National Stage application of PCT international application PCT/EP2018/067140, filed on Jun. 26, 2018 which claims the priority of French Patent Application No. 17 55907, filed Jun. 27, 2017, both of which are incorporated herein by reference in their entirety.

The present invention concerns stable dispersions comprising macroscopic drops of a dispersed fatty phase comprising at least one gelling agent and at least one non-volatile hydrocarbon oil. A further subject concerns compositions, particularly cosmetic compositions, containing said dispersions and uses thereof in the cosmetic field.

At the present time there exist dispersions of macroscopic drops of a fatty phase dispersed in an aqueous phase and notably described in applications WO 2012/120043, FR 2 972 367 and FR 2 976 824. These dispersions are obtained in particular using a microfluidic method.

The macroscopic nature of the drops allows compositions to be obtained provided with an attractive and distinguishing visual impact and having unique sensorial properties, affording an alternative to conventional usually white emulsions comprising dispersed phase droplets that are not visible to the naked eye.

Dispersions of macroscopic drops of this type have low mechanical strength however, possibly leading to shearing or fragmenting of the drops when transported. To overcome this drawback, it is known to place these dispersions in packaging known as "airless" packaging which restricts the uses thereof.

To remedy this issue, application WO 2017/046305 describes adding at least one gelling agent to the dispersed fatty phase, which allows stable dispersions to be obtained having high mechanical strength enabling the latter to withstand shearing or fragmenting of the macroscopic drops when transported.

Nonetheless, one shortcoming sometimes observed in the macroscopic dispersions of WO 2017/046305 is opacification of the continuous aqueous phase and/or adhering together of the drops and/or adhesion thereof onto the walls of the packaging.

Without wishing to be bound by any theory, the Applicant assumes that the opacification is associated with leakage of oil(s) and/or of gelling agent(s) from the dispersed phase towards the continuous aqueous phase.

For obvious reasons, these shortcomings are not desirable, at least for the reasons set forth below. With regard to attractiveness especially in the cosmetic field, visual impact is a major criterion of choice (and hence of purchase). In addition, the above-mentioned leakages may be accompanied by aggregation of the dispersed phase drops, again having a negative impact on the visual impact of the dispersion. This leakage is likely to cause escape of encapsulated active substance(s) which would be detrimental to the integrity of said active substance(s) and may even accentuate opacification and lead to adverse reactions with other active substances contained in the continuous aqueous phase. Yet the purpose of encapsulation is to preserve the integrity of an encapsulated active substance and even to make possible the use of active substances in one same composition that are not compatible with each other, whilst imparting a distinguishing and attractive visual impact for consumers. Finally, any change in the distribution of drop size and the presence of aggregates can lead to varying drop densities and therefore to non-homogeneous dose distribution.

There is therefore a need for novel dispersions comprising macroscopic drops which do not have the above-mentioned drawbacks.

More generally, the development of dispersions, particularly in the cosmetic field, that are increasingly more stable and visually attractive over time remains a constant objective.

It is therefore the objective of the present invention to provide stable dispersions of macroscopic drops in which phenomena of opacification of the continuous aqueous phase and/or adhesion of drops to packaging walls and/or drop aggregation are reduced and even overcome.

A further objective of the invention is to provide a stable dispersion of macroscopic drops allowing averted/prevented leakage of oil(s) and/or gelling agent(s) even of encapsulated active substance(s) from the dispersed phase towards the continuous aqueous phase, thereby preserving the integrity of said active substances and/or said drops and hence the stability of said dispersion over time.

The present invention therefore concerns a dispersion containing a dispersed phase comprising drops and a continuous aqueous phase, preferably in gel form, in which the drops comprise a fatty phase containing at least one gelling agent, and in which the fatty phase comprises at least one non-volatile hydrocarbon oil H1 containing more than 90%, preferably more than 95% of fatty acids having at least 18 carbon atoms, preferably at least 20 carbon atoms.

The dispersion of the invention has the advantage of being stable, particularly over time and during transport. By «stable» in the meaning of the present invention it is meant to designate the absence of creaming or sedimentation of the dispersed phase drops in the continuous phase, the absence of opacification of the continuous aqueous phase, the absence of drop aggregation and in particular the absence of drop coalescence or Ostwald ripening, and the absence of leakage of materials from the dispersed phase towards the continuous phase or conversely.

As will be seen from the examples described below, the use of at least one non-volatile hydrocarbon oil such as mentioned above in a dispersion of the invention allows the opacification phenomenon of the continuous aqueous phase, the leakage of materials particularly oil(s) and/or gelling agent(s) from the dispersed phase towards the continuous aqueous phase, the adhering of drops to the walls of packaging and/or drop aggregation to be reduced and even prevented. It is thereby possible to maintain and even improve the stability over time and visual impact of a dispersion of the invention.

The drops of the dispersion of the invention are macroscopic drops i.e. said drops are visible to the naked eye as opposed to microscopic drops that are not visible to the naked eye. Therefore, in one embodiment, at least 60%, even at least 70%, preferably at least 80% and better still at least 90% of the drops have a mean diameter $\overline{D}$ larger than or equal to 100 µm, even larger than or equal to 200 µm, better still larger than or equal to 300 µm, in particular larger than or equal to 400 µm, preferably larger than or equal to 500 µm, even larger than or equal to 1 000 µm, even between 100 µm and 3 000 µm, better still between 200 µm and 2 000 µm, in particular between 300 µm and 1 000 µm, better still between 500 µm and 3 000 µm, preferably between 1 000 µm and 2 000 µm, and in particular between 800 µm and 1 500 µm.

Advantageously, in a dispersion of the invention, the drops having a diameter larger than or equal to 100 µm, even larger than or equal to 200 µm, better still larger than or equal to 300 µm, in particular larger than or equal to 400 µm, preferably larger than or equal to 500 µm, even larger than or equal to 1 000 µm, even between 100 µm and 3 000 µm, better still between 200 µm and 2 000 µm, in particular between 300 µm and 1 000 µm, better still between 500 µm and 3 000 µm, preferably between 1 000 µm and 2 000 µm, and in particular between 800 µm and 1 500 µm, represent a volume of 60% or more, even 70% or more, preferably 80% or more and better still of 90% or more of the total volume of the dispersed phase.

Determination of the volume of drops having a particular diameter relative to the total volume of the dispersed phase lies within the general knowledge of persons skilled in the art, in particular regarding the method used to measure diameter described below.

In the present invention, the above-mentioned dispersions can indifferently be designated by the term "emulsions".

In addition, the drops advantageously have apparent monodispersity (i.e. they are seen as spheres of identical diameter). Advantageously, the drops are substantially spherical.

Temperature and Pressure

Unless otherwise stated in the remainder hereof, the temperature is considered to be ambient temperature (e.g. T=25° C.±2° C.) and pressure is atmospheric (760 mm de Hg, i.e. $1.013 \times 10^5$ Pa or $10^{13}$ mbar).

Viscosity

The viscosity of the compositions of the invention can vary widely allowing varied textures to be obtained.

In one embodiment, a dispersion of the invention has viscosity from 1 mPa·s to 500 000 mPa·s, preferably from 10 mPa·s to 300 000 mPa·s, more preferably from 400 mPa·s to 100 000 mPa·s, and further preferably from 1 000 mPa·s to 30 000 mPa·s, such as measured at 25° C.

Viscosity is measured at ambient temperature and ambient pressure using the method described in WO2017046305.

Continuous Aqueous Phase

As previously indicated, the dispersions of the invention comprise a continuous aqueous phase preferably in gel form.

Advantageously, the continuous phase is not solid at ambient temperature and ambient pressure i.e. it is able to flow under its own weight.

In one embodiment, the aqueous phase has viscosity of between 400 mPa·s and 100 000 mPa·s, preferably between 800 mPa·s and 30 000 mPa·s, such as measured at 25° C.

This viscosity is measured using the above-described method.

The continuous phase of the dispersions comprises water.

In addition to distilled or deionized water, water suitable for the invention can also be natural spring water or floral water.

In one embodiment, the weight percentage of water in the continuous aqueous phase is at least 30%, preferably at least 40%, in particular at least 50%, better still at least 60%, in particular between 70% and 98%, and preferably between 75% and 95%, relative to the total weight of said continuous phase.

The continuous aqueous phase of the dispersion of the invention may also comprise at least one base. It may comprise a single base or a mixture of several different bases. The presence of at least one base in said continuous aqueous phase contributes in particular to enhancing the viscosity thereof.

In one embodiment, the base contained in the aqueous phase is a mineral base.

In one embodiment, the mineral base is selected from the group formed of alkali metal hydroxides and alkaline-earth metal hydroxides.

Preferably, the mineral base is a hydroxide of alkali metals and NaOH in particular.

In one embodiment, the base contained in the aqueous phase is an organic base. Among organic bases, mention can be made for example of ammonia, pyridine, triethanolamine, aminomethyl propanol, or triethylamine.

A dispersion of the invention can comprise from 0.01 weight % to 10 weight %, preferably from 0.01 weight % to 5 weight %, and more preferably from 0.02 weight % to 1 weight % of base, preferably of mineral base and NaOH in particular, relative to the total weight of said dispersion.

In one embodiment, the dispersions of the invention do not comprise a surfactant.

In one embodiment, the dispersions of the invention do not comprise glyceryl trioctanoate, glycerol tricaprylate/caprate, or mixture thereof.

Shell of the Drops

In a first embodiment, the drops of a dispersion of the invention are free of shell or membrane, in particular of a polymeric membrane or formed by interfacial polymerization. In particular, the drops of a dispersion of the invention are not stabilized by means of a coacervate membrane (of the type anionic polymer (carbomer)/cationic polymer (amodimethicone)).

In other words, the contact between the continuous aqueous phase and dispersed fatty phase is direct.

In another embodiment, the drops of the dispersed phase also comprise a shell. Preferably, this shell comprises at least one anionic polymer and at least one cationic polymer.

In one preferred embodiment, the drops of the invention are surrounded by a shell (or membrane) comprising at least one anionic polymer and at least one cationic polymer.

In the invention, the drops obtained can have a very thin shell, in particular having a thickness of less than 1% of the diameter of the drops.

The thickness of the shell is therefore preferably less than 1 µm and hence too narrow to be measured using optical methods.

In one embodiment, the thickness of the shell of the drops is less than 1 000 nm, in particular from 1 to 500 nm, preferably less than 100 nm, advantageously less than 50 nm, preferably less than 10 nm.

Measurement of the shell thickness of the drops of the invention can be performed using Small-Angle X-ray Scattering, such as reported in Sato et al. J. Chem. Phys. 111, 1393-1401 (2007).

For this measurement, the drops are produced using deuterated water, then washed three times with deuterated oil e.g. deuterated oil of hydrocarbon type (octane, dodecane, hexadecane).

After washing, the drops are transferred into the Neutron cell to determine the spectrum I(q); q being the wave vector.

This spectrum is used to apply conventional analytical methods (REF) to determine the thickness of the hydrogenated (non-deuterated) shell.

In one embodiment, the shell surrounding the drops of the dispersed phase is rigidified thereby imparting good resistance to the drops and reducing even preventing coalescence thereof.

This shell is typically formed by coacervation, i.e. by precipitation of polymers having opposite charges. Within a coacervate, the bonds linking the charged polymers together are of ionic type, and are generally stronger than the bonds within a membrane of surfactant type.

The shell is formed by coacervation of at least two polymers having charges of opposite polarity (or polyelectrolyte) and preferably in the presence of a first polymer of cationic type, and a second polymer differing from the first polymer and of anionic type. These two polymers act as rigidifying agents of the membrane.

The formation of the coacervate between these two polymers can be caused by modifying the conditions of the reaction medium (temperature, pH, reagent concentrations, etc.).

A coacervation reaction results from neutralisation of these two polymers having charges of opposite polarity, and allows the formation of a membrane structure via electrostatic interactions between the anionic polymer and cationic polymer. The membrane thus formed around each drop typically forms a shell which fully encapsulates the core of the drop, thereby isolating the core of the drop from the continuous aqueous phase.

In the presence of a shell of coacervate type, derived in particular from use of amodimethicone, the advantageous effects attached to the use of an oil H1, in particular if it is a vegetable oil, are unexpected. It is known that amodimethicone has lack of compatibility with vegetable oils, which can lead to poor solubilisation of amodimethicone, to imperfect coacervate membrane quality and hence to exacerbated coalescence of the drops. In other words, the present invention goes against preconceived technical opinion whereby the use of a vegetable oil can be detrimental to the stability of a dispersion stabilized by a coacervate membrane resulting from the use of amodimethicone in particular. These problems are further accentuated when a dispersion is considered comprising drops of macroscopic size.

On the contrary, and as follows from the examples below, it is observed that the presence of a coacervate membrane has advantageous effects in terms of reducing the opacification phenomenon of the continuous aqueous phase and reducing adhesion of drops onto the walls of packaging, and even drop aggregation, despite the use of a vegetable oil H1.

Anionic Polymer

In the present invention, by "polymer of anionic type" or «anionic polymer» it is meant a polymer comprising chemical functions of anionic type. The term anionic polyelectrolyte can also be used.

By "chemical function of anionic type", it is meant a chemical function AH capable of losing a proton to give a function A⁻. Depending on the conditions of the medium in which it is contained, a polymer of anionic type therefore comprises chemical functions in AH form, or else in the form of its conjugate base A⁻.

As examples of chemical functions of anionic type, mention can be made of the carboxylic acid functions —COOH, which may be present in the form of a carboxylate anion —COO⁻.

As examples of polymers of anionic type, mention can be made of any polymer formed by polymerization of monomers of which at least one part carries chemical functions of anionic type such as carboxylic acid functions. For example, such monomers are acrylic acid, maleic acid, or any ethylenically unsaturated monomer comprising at least one carboxylic acid function. It may be an anionic polymer for example comprising monomer units containing at least one chemical function of carboxylic acid type.

Preferably, the anionic polymer is hydrophilic i.e. soluble or dispersible in water.

Among the examples of polymer of anionic type suitable for implementing the invention, mention can be made of copolymers of acrylic acid or maleic acid with other monomers such as acrylamide, alkyl acrylates, $C_5$-$C_8$ alkyl acrylates, $C_{10}$-$C_{30}$ alkyl acrylates, $C_{12}$-$C_{22}$ alkyl methacrylates, methoxypolyethyleneglycol methacrylates, hydroxyester acrylates, crosspolymer acrylates, and mixtures thereof.

In the invention, a polymer of anionic type is preferably a carbomer such as described below. This polymer can also be a crosslinked acrylates/$C_{10-30}$ alkyl acrylate copolymer (INCI name: acrylates/$C_{10-30}$ alkyl acrylate Crosspolymer).

In one embodiment, the shell of the drops comprises at least one anionic polymer e.g. a carbomer.

In the invention and unless otherwise stated, by "carbomer" it is meant an optionally crosslinked homopolymer derived from polymerization of acrylic acid. It is therefore an optionally crosslinked poly(acrylic acid). Among the carbomers of the invention mention can be made of those marketed under the trade names Tego® Carbomer 340FD by Evonik, Carbopol® 981 by Lubrizol, Carbopol ETD 2050 by Lubrizol, or Carbopol Ultrez 10 by Lubrizol.

In one embodiment, by "carbomer" or "Carbopol®" it is meant an acrylic acid polymer of high molecular weight crosslinked with allyl sucrose or allyl ethers of pentaerythritol (Handbook of Pharmaceutical Excipients, $5^{th}$ Edition, pill). For example, it is Carbopol®910, Carbopol®934, Carbopol®934P, Carbopol®940, Carbopol®941, Carbopol®71G, Carbopol®980, Carbopol®971P or Carbopol®974P. In one embodiment, the viscosity of said carbomer is between 4 000 and 60 000 cP at 0.5% w/w.

Carbomers have other names: polyacrylic acids, carboxyvinyl polymers or carboxy polyethylenes.

A dispersion of the invention may comprise from 0.01 weight % to 5 weight %, preferably 0.05 to 2 weight %, and more preferably 0.1 to 0.5 weight % of anionic polymer(s), of carbomers in particular, relative to the total weight of said dispersion.

In the invention, the dispersions of the invention can comprise a carbomer and an acrylates/$C_{10-30}$ alkyl acrylate Crosspolymer.

The aqueous phase of the invention can also comprise at least one crosslinked polymer or at least one crosslinked copolymer, said crosslinked polymer or crosslinked copolymer comprising at least one unit derived from the polymerization of one of the following monomers: acrylic or methacrylic acid, alkyl acrylate or methacrylate having 1 to 30 carbon atoms, or the salts thereof.

This is notably the case when a dispersion of the invention comprises at least one fragrance such as defined below.

The aqueous phase can also comprise a mixture of crosslinked polymers or a mixture of crosslinked copolymers or a mixture of crosslinked polymer(s) and crosslinked copolymer(s).

In the invention, the term "unit derived from polymerization of a monomer" means that the polymer or copolymer is a polymer or copolymer obtained by polymerization or copolymer of said monomer.

In one embodiment, the crosslinked polymer or crosslinked copolymer is a crosslinked polyacrylate.

The crosslinked copolymers and polymers of the invention are anionic.

In one embodiment, the copolymer is a copolymer of unsaturated carboxylic acid and unsaturated $C_{1-30}$ alkyl carboxylate, preferably $C_1$-$C_4$. Said copolymer comprises at least one hydrophilic repeating unit of olefinic unsaturated carboxylic acid type and at least one hydrophobic repeating unit of the type ($C_1$-$C_{30}$) alkyl ester of unsaturated carboxylic acid.

Preferably, these copolymers are selected from among those in which the hydrophilic repeating unit of olefinic unsaturated carboxylic acid type corresponds to the monomer of following formula (I):

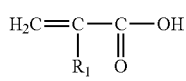

where: $R_1$ is H or $CH_3$ or $C_2H_5$, i.e. repeating units of acrylic acid, methacrylic acid or ethacrylic acid, and in which the hydrophobic repeating unit of the type ($C_1$-$C_{30}$) alkyl ester of unsaturated carboxylic acid corresponds to the monomer of following formula (II):

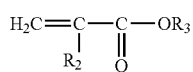

where: $R_2$ is H or $CH_3$ or $C_2H_5$ (i.e. acrylate, methacrylate or ethacrylate repeating units) and preferably H (acrylate repeating units) or $CH_3$ (methacrylate repeating units), $R_3$ being a $C_1$-$C_{30}$ alkyl radical, preferably $C_1$-$C_4$.

Among this type of copolymers, more particular use is made of those formed from a mixture of monomers comprising:

(i) essentially acrylic acid, (ii) an ester of formula (II) described above and where $R_2$ is H or $CH_3$, $R_3$ being an alkyl radical having 1 to 4 carbon atoms, (iii) and a crosslinking agent which is a well-known copolymerizable polyethylenic unsaturated monomer such as diallyl phthalate, trimethylolpropane tri(meth)acrylate, diallyl itaconate, diallyl fumarate, diallyl maleate, zinc (meth)acrylate, allyl (meth)acrylate, divinylbenzene, poly(ethylene glycol) dimethacrylate, methylene-bis-acrylamide, and castor oil.

In one embodiment, the crosslinked polymer or crosslinked copolymer is a polymer or copolymer of acrylic acid and/or methacrylic acid and/or of alkyl acrylate having 1 to 30 carbon atoms, preferably 1 to 4 carbon atoms, and/or of alkyl methacrylate having 1 to 30 carbon atoms, preferably 1 to 4 carbon atoms.

In one embodiment, the crosslinked copolymer is a crosslinked copolymer of methacrylic acid and alkyl acrylate having 1 to 4 carbon atoms, preferably 2 carbon atoms.

In the invention, and unless otherwise stated, by «crosslinked copolymer of methacrylic acid and alkyl acrylate having 1 to 4 carbon atoms», it is meant a crosslinked copolymer resulting from polymerization of a monomer of methacrylic acid and of a monomer of alkyl acrylate having 1 to 4 carbon atoms.

Preferably, in this copolymer, methacrylic acid represents from 20 weight % to 80 weight %, preferably 35 to 65 weight % of the total weight of the copolymer.

Preferably, in this copolymer, the alkyl acrylate represents from 15 weight % to 80 weight %, preferably 35 to 65 weight % of the total weight of the copolymer.

In particular, the alkyl acrylate is selected from among alkyl methacrylate, ethyl acrylate and butyl acrylate.

In one embodiment, the crosslinked polymer or crosslinked copolymer of the invention contained in the continuous aqueous phase is selected from the group formed by the following polymers or copolymers: Acrylates Copolymer, Acrylates crosspolymer-4, Acrylates crosspolymer-3, Polyacrylate-2 Crosspolymer and Polyacrylate-14 (INCI names).

Among said above polymers, particular preference in the present invention is given to products sold by LUBRIZOL under the trade names Fixate Superhold (INCI name=Polyacrylate-2 Crosspolymer), Fixate Freestyle Polymer (INCI name=Acrylates crosspolymer-3), Carbopol® Aqua SF1 (INCI name=Acrylates copolymer) and Carbopol® Aqua SF2 (INCI name=Acrylates crosspolymer-4).

Preferably, the crosslinked copolymer is Carbopol® Aqua SF1 (INCI name=Acrylates copolymer).

In one embodiment, the crosslinked copolymer is selected from among crosslinked copolymers of acrylic or methacrylic acid and alkyl acrylates having 1 to 4 carbon atoms.

In the invention, the dispersion of the invention may comprise from 0.1 weight % to 10 weight %, preferably 0.5 weight % to 8 weight %, and more preferably 1 weight % to 3 weight % of crosslinked polymer(s) or crosslinked copolymer(s) relative to the total weight of said dispersion.

In the invention, the dispersions of the invention may comprise a carbomer and a crosslinked copolymer Carbopol® Aqua SF1 (INCI name=Acrylates copolymer).

Cationic Polymer

In one embodiment, the drops and in particular the shell of said drops, also comprise a polymer of cationic type. They may also comprise several polymers of cationic type. This cationic polymer is the one mentioned above which forms the shell via coacervation with the anionic polymer.

In the present application, and unless otherwise stated, by "polymer of cationic type" or «cationic polymer» it is meant a polymer comprising chemical functions of cationic type. The term cationic polyelectrolyte can also be used.

Preferably, the cationic polymer is lipophilic or liposoluble.

In the present application, and unless otherwise stated, by "chemical function of cationic type", it is meant a chemical function B capable of capturing a proton to give a function $BH^+$. Depending on the conditions of the medium in which it is contained, the polymer of cationic type therefore comprises chemical functions in form B or else in form $BH^+$, its conjugate acid.

As examples of chemical functions of cationic type, primary, secondary and tertiary amine functions can be cited, optionally present in the form of ammonium cations.

As examples of polymers of cationic type, mention can be made of any polymer formed by polymerization of monomers at least one part of which carries chemical functions of cationic type, such as primary, secondary or tertiary amine functions.

Such monomers are aziridine for example, or any ethylenically unsaturated monomer comprising at least one primary, secondary or tertiary amine function.

Among the examples of cationic polymers suitable for implementing the invention, mention can be made of amodimethicone, a derivative of a silicone polymer (polydimethylsiloxane, also called dimethicone), modified by primary amine and secondary amine functions.

Derivatives of amodimethicone can also be cited, e.g. copolymers of amodimethicone, aminopropyl dimethicone, and more generally linear or branched silicone polymers comprising amine functions.

Mention can be made of the copolymers bis-isobutyl PEG-14/amodimethicone, Bis (C13-15 Alkoxy) PG-Amodimethicone, Bis-Cetearyl Amodimethicone and bis-hydroxy/methoxy amodimethicone.

Polymers can also be cited of polysaccharide type comprising amine functions, such as chitosan or the derivatives of guar gum (guar hydroxypropyltrimonium chloride).

Polymers can also be cited of polypeptide type comprising amine functions, such as polylysine.

Polymers of polyethyleneimine type can also be cited comprising amine functions, such as linear or branched polyethyleneimine.

In one embodiment, the drops and in particular the shell of said drops, comprise a cationic polymer which is a silicone polymer modified by a primary, secondary or tertiary amine function, such as amodimethicone.

In one embodiment, the drops and in particular the shell of said drops comprise amodimethicone.

In one particularly preferred embodiment, the cationic polymer meets the following formula:

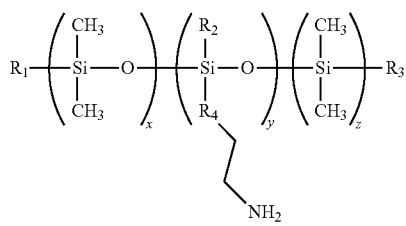

where:
$R_1$, $R_2$ and $R_3$ are each independently OH or $CH_3$;
$R_4$ is a —$CH_2$— group or —X—NH— group where X is a C3 or C4 divalent alkylene radical;
x is an integer of between 10 and 5 000, preferably between 30 and 1 000, more preferably between 80 and 300;
y is an integer of between 1 and 1 000, in particular between 2 and 1 000, preferably between 4 and 100, and better still between 5 and 20; and
z is an integer of between 0 and 10, preferably between 0 and 1, and better still it is 1.

In the above-mentioned formula, when $R_4$ is a group —X—NH—, X is linked to the silicon atom.

In the above-mentioned formula, $R_1$, $R_2$ and $R_3$ are preferably $CH_3$.

In the above-mentioned formula, $R_4$ is preferably a group —$(CH_2)_3$—NH—.

In the invention, each drop may comprise from 0.01% to 10%, preferably from 0.05% to 5% by weight of cationic polymer(s), of amodimethicone(s) in particular, relative to the total weight of the fatty phase.

In one embodiment, a decrease is seen in drop aggregation at contents of lipophilic cationic polymer(s), and of amodimethicone in particular, of between 0.15% and 0.8%, preferably between 0.25% and 0.6% by weight, relative to the weight of the fatty phase.

Fatty Phase

In the invention, the dispersions comprise a dispersed fatty phase, in drop form, comprising at least one gelling agent.

Gelling Agent

As previously indicated, the present invention is based on the presence, in the dispersed fatty phase, of at least one gelling agent. Said gelling agent differs from the anionic and cationic polymers described above.

In the invention and unless otherwise stated, by «gelling agent» it is meant an agent allowing an increase in the viscosity of the fatty phase of the drops of the dispersion devoid of said gelling agent, and allowing the gelled fatty phase to reach a final viscosity higher than 20 000 mPa·s, preferably higher than 50 000 mPa·s, more preferably higher than 100 000 mPa·s, and further preferably higher than 200 000 mPa·s.

Preferably, the viscosity of the fatty phase of the drops of the dispersion in the presence of said gelling agent is between 20 000 and 100 000 000 mPa·s, preferably between 50 000 and 1 000 000 mPa·s, and better still between 100 000 and 500 000 mPa·s, at 25° C.

The choice of gelling agent(s) is made with particular regard to the type of dispersed phase. Therefore, for obvious reasons of compatibility, the gelling agent is lipophilic.

In one embodiment, the gelling agent is chosen from among organic or mineral, polymeric or molecular lipophilic gelling agents; fats solid at ambient temperature and pressure; and mixtures thereof, and selected in particular from among waxes, pasty fats, butters, and mixtures thereof.

Lipophilic Gelling Agent(s)

The gelling agents able to be used in the invention can be organic or mineral, polymeric or molecular lipophilic gelling agents.

As mineral lipophilic gelling agent, mention can be made of optionally modified clays such as hectorites modified by $C_{10}$ to $C_{22}$ ammonium chloride, hectorite modified by distearyl dimethyl ammonium chloride such as the one marketed for example under the trade name Bentone 38V® by ELEMENTIS. Hectorite modified by distearyl dimethyl ammonium chloride can also be cited also known as quaternium-18 bentonite, e.g. the products marketed or produced under the trade names Bentone 34 by Rheox; Claytone XL, Claytone 34 and Claytone 40 marketed or produced by Southern Clay, modified clays known under the names benzalkonium and quaternium-18 bentonites and marketed or produced under the trade names HT, Claytone GR and Claytone PS by Southern Clay, clays modified by stearyldimethylbenzoylammonium chloride known as stearalkonium bentonites, such as those marketed or produced under the trade names Claytone APA and Claytone AF by Southern Clay, and Baragel 24 marketed or produced by Rheox.

Mention can also be made of pyrogenated silica optionally with hydrophobic surface treatment and having a particle size smaller than 1 μm. It is possible chemically to modify the surface of silica via chemical reaction generating a decrease in the number of silanol groups present on the silica surface. It is possible in particular to substitute silanol groups by hydrophobic groups: resulting in hydrophobic silica.

The hydrophobic groups can be:
trimethylsiloxyl groups, obtained in particular by treating pyrogenated silica in the presence of hexamethyldisilazane. Silicas thus treated are called «Silica silylate» in accordance with CTFA ($8^{th}$ Edition, 2000). They are marketed for example under the references Aerosil R812® by DEGUSSA, and CAB-O-SIL TS-530® by CABOT; or
dimethylsilyloxyl or polydimethylsiloxane groups, particularly obtained by treating pyrogenated silica in the presence of polydimethylsiloxane or dimethyldichlorosilane. Silicas thus treated are called «Silica dimethyl silylate» in accordance with CTFA ($8^{th}$ Edition, 2000). They are marketed for example under the references Aerosil R972® and Aerosil R974® by DEGUSSA, CAB-O-SIL TS-610® and CAB-O-SIL TS-720® by CABOT.

Hydrophobic pyrogenated silica particularly has a particle size that can be nanometric or micrometric e.g. ranging from about 5 to 200 nm.

Polymeric organic lipophilic gelling agents can be partly or fully crosslinked elastomeric organopolysiloxanes for example, of three-dimensional structure such as those marketed under the trade names KSG6®, KSG16® and KSG18® by SHIN-ETSU, Trefil E-505C® and Trefil E-506C® by DOW-CORNING, Gransil SR-CYC®, SR DMF10®, SR-DC556®, SR SCYC Gel®, SR DMF 10 Gel® and SR DC 556 Gel® by GRANT INDUSTRIES, SF 1204® and JK 113® by GENERAL ELECTRIC; ethylcellulose such as the one sold under the trade name Ethocel® by DOW CHEMICAL; galactomannans having from one to six and in particular two to four hydroxyl groups per monosaccharide unit, substituted by a saturated or unsaturated alkyl chain such as guar gum alkylated by $C_1$ to $C_6$ alkyl chains, in particular $C_1$ à $C_3$, and mixtures thereof. «Diblock», «Triblock» or «Radial» block copolymers of polystyrene/polyisoprene, polystyrene/polybutadiene type such as those marketed under the trade name Luvitol HSB® by BASF, of polystyrene/copoly(ethylene-propylene) type such as those marketed under the trade name Kraton® by SHELL CHEMICAL CO or of polystyrene/copoly(ethylene-butylene) type, mixtures of triblock and radial (star) copolymers in isododecane such as those marketed by PENRECO under the trade name Versagel® e.g. the mixture of butylene/ethylene/styrene triblock copolymer and ethylene/propylene/styrene star copolymer in isododecane (Versagel M 5960).

In one embodiment, the gelling agents able to be used in the invention can be selected from the group formed by polyacrylates; esters of sugar/polysaccharide and fatty acid(s), in particular esters of dextrin and fatty acid(s), esters of glycerol and fatty acid(s) or esters of inulin and fatty acid(s); polyamides, and mixtures thereof.

As lipophilic gelling agent, further mention can be made of polymers having a weight average molecular weight of less than 100 000, comprising a) a polymeric backbone having hydrocarbon repeating units provided with at least one heteroatom, and optionally b) at least one optionally functionalised pendant fatty chain and/or at least one optionally functionalised terminal fatty chain having 6 to 120 carbon atoms and being linked to these hydrocarbon repeating units such as described in applications WO 02/056847, WO 02/47619, in particular polyamide resins (particularly comprising alkyl groups having 12 to 22 carbon atoms) such as described in U.S. Pat. No. 5,783,657.

As an example of polyamide resin able to be used in the present invention, UNICLEAR 100 VG® can be cited marketed by ARIZONA CHEMICAL.

It is also possible to use silicone-containing polyamides of polyorganosiloxane type such as those described in U.S. Pat. Nos. 5,874,069, 5,919,441, 6,051,216 and 5,981,680.

These silicone-containing polymers can belong to the two following families:
 polyorganosiloxanes comprising at least two groups capable of setting up hydrogen interactions, these two groups being positioned on the polymer chain, and/or
 polyorganosiloxanes comprising at least two groups capable of setting up hydrogen interactions, these two groups being positioned on grafts or branches.

Among the lipophilic gelling agents able to be used in the invention, further mention can be made of the esters of dextrin and fatty acids, such as dextrin palmitates.

In one embodiment, the ester of dextrin and fatty acid(s) of the invention is a mono- or poly-ester of dextrin and of at least one fatty acid meeting following formula (II):

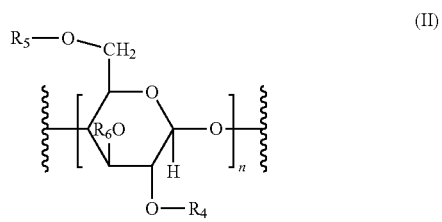

where:
 n is an integer ranging from 2 to 200, preferably ranging from 20 to 150 and in particular ranging from 25 to 50,
 the radicals $R_4$, $R_5$ and $R_6$, the same or different, are selected from among hydrogen or an acyl —$COR_a$ group wherein the radical $R_a$ is a saturated or unsaturated, linear or branched hydrocarbon radical having 5 to 50, preferably 5 to 25 carbon atoms,
 provided that at least one of said radicals $R_4$, $R_5$ or $R_6$ differs from hydrogen.

In one embodiment, $R_4$, $R_5$ and $R_6$ are each independently H or acyl —$COR_a$ group wherein $R_a$ is a hydrocarbon radical such as previously defined, provided that at least two of said radicals $R_4$, $R_5$ or $R_6$ are the same and differ from hydrogen.

In one embodiment, when the radicals $R_4$, $R_5$ and $R_6$, the same or different, are a —$COR_a$ radical, they can be selected from among caprylyl, caproyl, lauroyl, myristyl, palmityl, stearyl, eicosanyl, docosanoyl, isovaleryl, ethyl-2 butyryl, ethylmethylacetyl, isoheptanyl, ethyl-2 hexanyl, isononanyl, isodecanyl, isotridecanyl, isomyristyl, isopalmityl, isostearyl, isohexanyl, decenyl, dodecenyl, tetradecenyl, myristyl, hexadecenoyl, palmitoleyl, oleyl, elaidyl, eicosenyl, sorbyl, linoleyl, linolenyl, punicyl, arachidonyl, stearoyl radicals, and mixtures thereof.

Among the esters of dextrin and fatty acid(s) mention can be made for example of dextrin palmitates, dextrin myristates, dextrin palmitates/ethylhexanoates and mixtures thereof.

The esters can particularly be cited of dextrin and fatty acid(s) marketed under the trade names Rheopearl® KL2 (INCI name: dextrin palmitate), Rheopearl® TT2 (INCI name: dextrin palmitate ethylhexanoate), and Rheopearl® MKL2 (INCI name: dextrin myristate) by Miyoshi Europe.

Particular mention can be made of the esters of inulin and fatty acid(s) marketed under the trade names Rheopearl® ISK2 or Rheopearl® ISL2 (INCI name: Stearoyl Inulin) by Miyoshi Europe.

In one embodiment, the gelling agent is selected from among the polyacrylates resulting from polymerization of $C_{10}$-$C_{30}$ alkyl acrylate(s), preferably $C_{14}$-$C_{24}$, alkyl acrylate(s), and more preferably $C_{18}$-$C_{22}$ alkyl acrylate(s).

In one embodiment, the polyacrylates are polymers of acrylic acid esterified with a fatty alcohol in which the saturated carbon chain comprises from 10 to 30 carbon atoms, preferably 14 to 24 carbon atoms, or a mixture of said fatty alcohols. Preferably, the fatty alcohol comprises 18 carbon atoms or 22 carbon atoms.

Among the polyacrylates, more particular mention can be made of stearyl polyacrylate, behenyl polyacrylate. Preferably, the gelling agent is stearyl polyacrylate or behenyl polyacrylate.

Particular mention can be made of the polyacrylates marketed under the trade names Interlimer® (INCI name: Poly $C_{10}$-$C_{30}$ alkyl acrylate), especially Interlimer® 13.1 and Interlimer® 13.6, by Airproducts.

In one embodiment, the gelling agent is an ester of glycerol and fatty acid(s), in particular a mono-, di- or triester of glycerol and fatty acid(s). Typically, said ester of glycerol and fatty acid(s) can be used alone or in a mixture.

In the invention, it can be an ester of glycerol and of a fatty acid, or an ester of glycerol and a mixture of fatty acids.

In one embodiment, the fatty acid is selected from the group formed by behenic acid, isooctadecanoic acid, stearic acid, eicosanoic acid, and mixtures thereof.

In one embodiment, the ester of glycerol and fatty acid(s) has following formula (III):

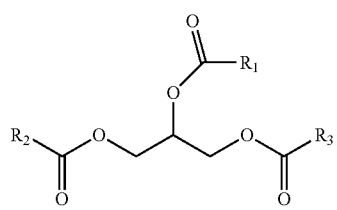

where: $R_1$, $R_2$ and $R_3$ are each independently selected from among H and a saturated alkyl chain having 4 to 30 carbon atoms, at least one of $R_1$, $R_2$ and $R_3$ differing from H.

In one embodiment, $R_1$, $R_2$ and $R_3$ are different.

In one embodiment, $R_1$, $R_2$ and/or $R_3$ are a saturated alkyl chain having from 4 to 30 carbon atoms, preferably 12 to 22 and more preferably 18 to 22 carbon atoms.

In one embodiment, the ester of glycerol and fatty acid(s) corresponds to a compound of formula (III) where $R_1$=H, $R_2$=$C_{21}H_{43}$ and $R_3$=$C_{19}H_{40}$.

In one embodiment, the ester of glycerol and fatty acid(s) corresponds to a compound of formula (III) where $R_1$=$R_2$=$R_3$=$C_{21}H_{43}$.

In one embodiment, the ester of glycerol and fatty acid(s) corresponds to a compound of formula (III) where $R_1$=$R_2$=H, and $R_3$=$C_{19}H_{40}$.

In one embodiment, the ester of glycerol and fatty acid(s) corresponds to a compound of formula (III) where $R_1$=$R_2$=H, and $R_3$=$C_{17}H_{35}$.

Particular mention can be made of the esters of glycerol and fatty acid(s) marketed under the trade names Nomcort HK-G (INCI name: Glyceryl behenate/eicosadioate) and Nomcort SG (INCI name: Glyceryl tribehenate, isostearate, eicosadioate), by Nisshin Oillio.

Waxe(s)

By «wax» in the meaning of the invention it is meant a lipophilic compound, solid at ambient temperature (25° C.), having reversible solid/liquid state change and a melting point of 30° C. or higher and possibly reaching 120° C.

The protocol for measuring this melting point is described below.

The waxes able to be used in a composition of the invention can be selected from among waxes that are solid, deformable or non-deformable at ambient temperature, of animal, vegetable, mineral or synthetic origin, and mixtures thereof.

Particular use can be made of hydrocarbon waxes such as beeswax, lanolin wax, Chinese insect waxes; rice wax, Carnauba wax, Candelilla wax, Ouricury wax, Alfa wax, cork fibre wax, sugar cane wax, Japan wax and sumac wax; montan wax, microcrystalline waxes, paraffins and ozokerite; polyethylene waxes, waxes obtained via Fischer-Tropsch synthesis and waxy copolymers and the esters thereof.

Waxes can particularly be cited that are marketed under the trade names Kahlwax®2039 (INCI name: Candelilla cera) and Kahlwax®6607 (INCI name: Helianthus Annuus Seed Wax) by Kahl Wachsraffinerie; Casid HSA (INCI name: Hydroxystearic Acid) by SACI CFPA, Performa®260 (INCI name: Synthetic wax) and Performa®103 (INCI name: Synthetic wax) by New Phase, and AJK-CE2046 (INCI name: Cetearyl alcohol, dibutyl lauroyl glutamide, dibutyl ethylhaxanoyl glutamide) by Kokyu Alcohol Kogyo.

Mention can also be made of waxes obtained by catalytic hydrogenation of animal or vegetable oils having $C_8$-$C_{32}$ linear or branched fatty chains.

Among these, particular mention is made of hydrogenated jojoba oil, hydrogenated sunflower seed oil, hydrogenated castor oil, hydrogenated copra oil and hydrogenated lanolin oil, di-(trimethylol-1,1,1 propane) tetrastearate sold under the trade name «HEST 2T-4S» by HETERENE, di-(trimethylol-1,1,1 propane) tetrabehenate sold under the trade name HEST 2T-4B by HETERENE.

It is also possible to use waxes obtained by transesterification and hydrogenation of vegetable oils such as castor or olive oil e.g. the waxes sold under the trade names Phytowax ricin 16L64® and 22L73® and Phytowax Olive 18L57 by SOPHIM. Said waxes are described in application FR2792190.

It is also possible to use silicone waxes that can advantageously be substituted polysiloxanes, preferably with low melting point.

Among commercially available silicone waxes of this type particular mention is made of those sold under the trade names Abilwax 9800, 9801 or 9810 (GOLDSCHMIDT), KF910 and KF7002 (SHIN ETSU), or 176-1118-3 and 176-11481 (GENERAL ELECTRIC).

The silicone waxes able to be used can also be alkyl or alkoxydimethicones such as the following commercial products: Abilwax 2428, 2434 and 2440 (GOLDSCHMIDT), or VP 1622 and VP 1621 (WACKER), and ($C_{20}$-$C_{60}$) alkyldimethicones, in particular ($C_{30}$-$C_{45}$) alkyldimethicones such as the silicone wax sold under the trade name SF-1642 by GE-Bayer Silicones.

It is also possible to use hydrocarbon waxes modified by silicone- or fluorine-containing groups e.g: siliconyl candelilla, siliconyl beeswax and Fluorobeeswax by Koster Keunen.

The waxes can also be selected from among fluorinated waxes.

Butter(s) or Pasty Fats

By «butter» (also called «pasty fat») in the meaning of the present invention, it is meant a lipophilic fatty compound having reversible solid/liquid state change and which at the temperature of 25° C. and atmospheric pressure (760 mm Hg) has a liquid fraction and a solid fraction. In other words, the start melting point of the pasty compound can be lower than 25° C. The liquid fraction of the pasty compound measured at 25° C. can represent 9% to 97% by weight of the compound. This liquid fraction at 25° C. preferably represents between 15% and 85%, more preferably between 40 and 85% by weight. Preferably, the butter(s) have an end melting point lower than 60° C. Preferably, the butter(s) have hardness lower than or equal to 6 MPa.

Preferably, the butters or pasty fats in solid state display anisotropic crystalline organisation visible under X-ray observation.

In the meaning of the invention, the melting point corresponds to the temperature of the most endothermic peak observed under differential scanning calorimetry (DSC) such as described in standard ISO 11357-3; 1999. The melting point of a paste or wax can be measured using a differential scanning calorimeter (DSC), e.g. the calorimeter sold under the reference "DSC Q2000" by TA Instruments.

Regarding measurement of melting point and determination of end melt temperature, the protocols for preparing samples and measurement are such as those described in WO2017046305.

The liquid fraction of the butter (or pasty fat) by weight at 25° C. is equal to the ratio between the enthalpy of fusion consumed at 25° C. and the enthalpy of fusion of the butter. The enthalpy of fusion of the butter or pasty compound is the enthalpy consumed by the compound to change from the solid state to the liquid state.

The butter is said to be in the solid state when the entirety of its mass is in solid crystalline form. The butter is said to be in the liquid state when the entirety of its mass is in liquid form. The enthalpy of fusion of butter is equal to the integral of the whole fusion curve obtained with the above-mentioned calorimeter, with a temperature rise of 5° C. or 10° C. per minute, as per standard ISO 11357-3:1999. The enthalpy of fusion of butter is the amount of energy needed for the compound to change from the solid state to the liquid state. It is expressed as J/g.

The enthalpy of fusion consumed at 25° C. is the amount of energy absorbed by the sample to change from the solid state to its state at 25° C. composed of a liquid fraction and a solid fraction. The liquid fraction of butter measured at 32° C. preferably represents 30 weight % to 100 weight % of the compound, preferably 50% to 100%, further preferably 60 to 100 weight % of the compound. When the liquid fraction of butter measured at 32° C. is equal to 100%, the temperature at the end of the melt range of the pasty compound is lower than or equal to 32° C. The liquid fraction of butter measured at 32° C. is equal to the ratio between the enthalpy of fusion consumed at 32° C. and the enthalpy of fusion of the butter. The enthalpy of fusion consumed at 32° C. is calculated in the same manner as the enthalpy of fusion consumed at 23° C.

Regarding measurement of hardness, the protocols for preparation of samples and measurement are such as described in WO2017046305.

The pasty fat or butter can be selected from among synthetic compounds and compounds of vegetable origin. A pasty fat can be obtained via synthesis from starting products of vegetable origin.

The pasty fat is advantageously selected from among:
lanoline and derivatives thereof such as lanoline alcohol, oxyethylenated lanolines, acetylated lanoline, esters of lanolin such as isopropyl lanolate, oxypropylenated lanolines,
polymer or non-polymer silicone compounds such as polydimethysiloxanes of high molecular weight, polydimethysiloxanes with side chains of alkyl or alkoxy type having 8 to 24 carbon atoms, particularly stearyl dimethicones,
polymer or non-polymer fluorinated compounds,
vinyl polymers, in particular
homopolymers of olefins,
copolymers of olefins,
homopolymers and copolymers of hydrogenated dienes,
linear or branched oligomers, homo- or copolymers of alkyl (meth)acrylates preferably having a $C_8$-$C_{30}$ alkyl group,
oligomers, homo- and copolymers of vinyl esters having $C_8$-$C_{30}$ alkyl groups,
oligomers, homo- and copolymers of vinyl ethers having $C_8$-$C_{30}$ alkyl groups,
liposoluble polyethers resulting from polyetherification between one or more $C_2$-$C_{100}$ diols, preferably $C_2$-$C_{50}$, esters and polyesters, and
mixtures thereof.

In one preferred embodiment, the particular butter(s) are of vegetable origin such as those described in Ullmann's Encyclopedia of Industrial Chemistry («Fats and Fatty Oils», A. Thomas, published on 15 Jun. 2000, D01: 10.1002/14356007.a10_173, point 13.2.2.2. Shea Butter, Borneo Tallow, and Related Fats (Vegetable Butters)).

Particular mention can be made of C10 to C18 triglycerides (INCI name: C10-18 Triglycerides) comprising a liquid fraction and solid fraction at a temperature of 25° C. and at atmospheric pressure (760 mm Hg), shea butter, Nilotica shea butter (*Butyrospermum parkii*), Galam butter (*Butyrospermum parkii*), Borneo butter or fat or tengkawang tallow (*Shorea stenoptera*), Shorea butter, Illipe butter, Madhuca butter or Bassia Madhuca longifolia, mowrah butter (*Madhuca latifolia*), Katiau butter (*Madhuca mottleyana*), Phulwara butter (*M. butyracea*), mango butter (*Mangifera indica*), Murumuru butter (*Astrocatyum murumuru*), Kokum butter (*Garcinia indica*), Ucuuba butter (*Virola sebifera*), Tucuma butter, Painya butter (Kpangnan) (*Pentadesma butyracea*), coffee butter (*Coffea arabica*), apricot butter (*Prunus Armeniaca*), Macadamia butter (*Macadamia temifolia*), grapeseed butter (*Vitis vinifera*), avocado butter (*Persea gratissima*), olive butter (*Olea europaea*), sweet almond butter (*Prunus amygdalus dulcis*), cocoa butter (*Theobroma cacao*) and sunflower seed butter, butter having the INCI name Astrocaryum Murumuru Seed Butter, butter having the INCI name Theobroma Grandiflorum Seed Butter, and butter having the INCI name Irvingia Gabonensis Kernel Butter, the esters of jojoba (mixture of hydrogenated jojoba oil and wax—INCI name: Jojoba esters) and the ethyl esters of shea butter (INCI name: Shea butter ethyl esters), and mixtures thereof.

Among the gelling agents of the invention mention can also be made of THIXCIN® R by Elementis Specialties (INCI: Trihydroxystearin) or Estogel E by PolymerExpert (Proposed INCI name: Castor oil/IPDI Copolymer, Caprylic Capric triglyceride, Castor oil).

Preferably, the gelling agent is selected from among dextrin palmitates.

Advantageously, a fatty phase gelling agent of the invention is a heat-sensitive gelling agent, namely which reacts to heat, and in particular a gelling agent solid at ambient temperature and liquid at a temperature higher than 40° C., preferably higher than 50° C.

Advantageously, a fatty phase gelling agent of the invention is a thixotropic gelling agent or able to impart thixotropic behaviour to the solution containing the same. Said thixotropic gelling agent is selected in particular from among optionally hydrophobic-treated pyrogenated silicas described in the foregoing.

In one embodiment, a dispersion of the invention can comprise from 0.1% to 75%, preferably 0.5% to 60%, in particular 1% to 40%, better still 1.5% to 20%, and most preferably 1% to 4% by weight of gelling agent(s) relative to the total weight of the dispersion.

In the invention, a dispersion of the invention can comprise from 0.5% to 99%, preferably 1% to 70%, more preferably 1.5% to 50%, further preferably 2% to 40%, in particular 2.5% to 30%, and most preferably 10% to 20% by weight of gelling agent(s) relative to the total weight of the fatty phase.

As follows from the examples below, an increase in the content of gelling agent(s), particularly of RHEOPEARL KL2, contributes towards further reducing the phenomenon of drop aggregation.

Oils

Oil H1

A dispersion of the invention requires the use in the fatty phase of at least one non-volatile hydrocarbon oil H1 containing more than 90%, preferably more than 95% of fatty acids having chain lengths of 18 carbon atoms or more, preferably 20 carbon atoms or more.

Preferably, more than 90%, and preferably more than 95% of the fatty acids of the non-volatile hydrocarbon oil have a chain length of between $C_{18}$ and $C_{36}$, preferably between $C_{20}$ and $C_{28}$, and better still between $C_{20}$ and $C_{22}$.

By «oil» is meant a fat liquid at ambient temperature (25° C.).

The chains of the fatty acids of the non-volatile hydrocarbon oil H1 are linear or branched, preferably linear, and saturated or unsaturated, preferably unsaturated, even polyunsaturated.

By "unsaturated fatty acid" in the meaning of the present invention it is meant a fatty acid comprising at least one double bond. It is more particularly a long chain fatty acid i.e. having at least 18, preferably 20 carbon atoms. The unsaturated fatty acids can be in acid form, or salt form e.g. their calcium salt, or in the form of derivatives in particular ester(s) of fatty acid(s).

By «non-volatile» it is meant an oil having a vapour pressure at ambient temperature and atmospheric pressure that is non-zero and lower than 0.02 mm Hg (2.66 Pa) and better still lower than $10^{-3}$ mm Hg (0.13 Pa).

Particularly suitable for the invention are unsaturated fatty acids having 18 to 36, preferably 20 to 28, more preferably 20 to 22 carbon atoms, in particular unsaturated even polyunsaturated fatty acids particularly Δ-5 and/or Δ-13 fatty acids.

Among the unsaturated fatty acids of the Δ-5 series, particular mention can be made of monounsaturated eicosenoic acid having 20 carbon atoms and one unsaturation (20:1, Δ-5), monounsaturated docosanoic acid having 22 carbon atoms and one unsaturation (22:1, Δ-5) polyunsaturated docosadienoic acid having 22 carbon atoms and two unsaturations (22:2, Δ 5).

Among unsaturated fatty acids of the Δ-13 series, monounsaturated docosanoic acid can be cited having 22 carbon atoms and one unsaturation (22:1, Δ-13).

In the meaning of the invention, the nomenclature «Δx» (or «delta-x») concerns unsaturated fatty acids for which each double bond is indicated by the sign Δ and followed by the position of the double bond along the aliphatic chain of the fatty acid from the —COOH carboxylic end of the molecule.

Preferably, a non-volatile hydrocarbon oil of the invention comprises a mixture of monounsaturated and polyunsaturated fatty acids.

Preferably, a non-volatile hydrocarbon oil of the invention comprises more than 90%, and preferably more than 95%, of fatty acids selected from among oleic acid, in particular of type (C18:1, Δ-9), eicosenoic acid in particular of type (C20:1, Δ-5), docosanoic acid in particular of type (C22:1, Δ-5) and/or (C22:1, Δ-13), docosadienoic acid in particular of type (C22:2, Δ 5), and mixtures thereof, and better still eicosenoic acid, docosanoic acid and/or docosadienoic acid, and mixtures thereof.

Preferably, the non-volatile hydrocarbon oil H1 is selected from among vegetable oils. In one embodiment, the dispersion of the invention comprises several oils H1 of which at least one is a vegetable oil. In one embodiment, the dispersion of the invention comprises several oils H1 selected from among vegetable oils.

Preferably, the non-volatile hydrocarbon oil H1 comprises less than 10%, preferably less than 5%, and is even devoid of fatty acid having a chain length shorter than 18 carbon atoms, and better still shorter than 20 carbon atoms.

Preferably, the non-volatile hydrocarbon oil H1 comprises less than 10%, preferably less than 5% and is even devoid of saturated fatty acid.

For example, as non-volatile hydrocarbon oils H1 of the invention, mention can be made of jojoba oil, flax oil, Perilla oil, Inca Inchi oil, rosehip seed oil, rapeseed oil, hemp oil, sweet almond oil, corn oil, apricot oil, castor oil, Meadowfoam oil (INCI: Limnanthes Alba (Meadowfoam) Seed Oil) and mixtures thereof, preferably jojoba oil and/or Meadowfoam oil, and better still Meadowfoam oil.

Meadowfoam oil has a particular fatty acid composition as described in the table below:

| Fatty acid composition | Composition (in %) | | General formula |
|---|---|---|---|
| C20:1 Δ-5 | 58-64 | | <br>C20:1 (Δ5) |
| C22:1 Δ-5 | 3-6 | 13-20 | <br>C22:1 (Δ5) |
| C22:1 Δ-13 | 10-14 | | <br>C22:1 (Δ13) |

| Fatty acid composition | Composition (in %) | General formula |
|---|---|---|
| C22:2 Δ-5 and Δ-13 | 15-21 |  C22:2 (Δ5 Δ13) |
| Total | 100 | |

For example, Meadowfoam oil is marketed by Nikon Chemicals under the trade name NIKKOL Meadowfoam Oil, or by Elementis Specialties under the trade name FANCOR® MEADOWFOAM SEED OIL.

The use of non-volatile hydrocarbon oils H1, in particular vegetable oils and particularly Meadowfoam oil in compositions and especially cosmetic compositions is known. However, it has never been observed that their use in a dispersed fatty phase of macroscopic drops is able to have advantageous effects in terms of reducing opacification of the continuous aqueous phase and/or adhesion of drops onto walls of packaging and/or drop aggregation.

Advantageously, the fatty phase of a dispersion of the invention comprises between 1% and 50%, preferably between 5% and 40%, in particular between 10% and 30%, better still between 16% and 20% by weight of oil(s) H1 relative to the total weight of said fatty phase.

Oil H2

In one embodiment, the fatty phase of the dispersion of the invention also comprises at least one oil H2 differing from the above-mentioned oil H1.

The presence of oil H2 can be advantageous to impart different sensorial properties to the dispersion of the invention or to ensure the use of a particular raw material being for example non-soluble in oil H1. This is particularly the case when oil H1 is a vegetable oil and the macroscopic drops of the dispersion of the invention comprise a shell derived in particular from the use of amodimethicone. As mentioned above, amodimethicone lacks compatibility with vegetable oils. Oil H2 is therefore preferably an oil in which the cationic polymer is soluble. Oil H2 is therefore advantageously compatible with the cationic polymer and therefore corresponds to a good solvent of the cationic polymer.

As H2 oils able to be used in the composition of the invention, mention can be made for example of:
  hydrocarbon oils of animal origin, such as perhydrosqualene and squalane;
  synthetic esters and ethers particularly of fatty acids, such as oils of formulas $R_1COOR_2$ et $R_1OR_2$ where $R_1$ represents the remainder of a $C_8$ to $C_{29}$ fatty acid, and $R_2$ is a $C_3$ to $C_{30}$ hydrocarbon chain whether or not branched e.g. Purcellin oil, isononyl isononanoate, isodecyl neopentanoate, isopropyl myristate, ethyl-2-hexyl palmitate, octyl-2-dodecyl stearate, octyl-2-dodecyl erucate, isostearyl isostearate; hydroxylated esters such as isostearyl lactate, octyl hydroxystearate, octyldodecyl hydroxystearate, diisostearyl-malate, triisocetyl citrate, heptanoates, octanoates, fatty alcohol decanoates; polyol esters such as propylene glycol dioctanoate, neopentylglycol diheptanoate and diethyleneglycol diisononanoate; and the esters of pentaerythritol such as pentaerythrityl tetrabehenate (DUB PTB) or pentaerythrityl tetraisostearate (Prisorine 3631);
  linear or branched hydrocarbons of mineral or synthetic origin, such as volatile or non-volatile paraffin oils and derivatives thereof, vaseline, polydecenes, hydrogenated polyisobutene such as Parleam oil;
  silicone oils e.g. polydimethylsiloxanes (PDMS) volatile or non-volatile having a linear or cyclic silicone chain, liquid or pasty at ambient temperature, particularly cyclopolydimethylsiloxanes (cyclomethicones) such as cyclohexasiloxane and cyclopentasiloxane; polydimethylsiloxanes (or dimethicones) comprising alkyl, alkoxy or phenyl groups, either pendant or at the end of the silicone chain, groups having 2 to 24 carbon atoms; phenylated silicones such as phenyltrimethicones, phenyldimethicones, phenyltrimethylsiloxydiphenyl-siloxanes, diphenyl-dimethicones, diphenylmethyldiphenyl trisiloxanes, 2-phenylethyltrimethylsiloxysilicates, and polymethylphenylsiloxanes;
  fatty alcohols having 26 carbon atoms e.g. cetyl alcohol, stearyl alcohol and mixture thereof (cetostearyl alcohol), or octyldodecanol;
  partially hydrocarbon- and/or silicone-containing fluorinated oils such as those described in document JP-A-2-295912;
  and mixtures thereof.

In one preferred embodiment, the fatty phase of the dispersion of the invention comprises a mixture between at least one oil H1 and at least one oil H2 differing from above-mentioned oil H1.

In one embodiment, the weight ratio between the amount of oil(s) H1 and the amount of oil(s) H2 ranges from 0.01 to 1, preferably from 0.05 to 0.66, in particular from 0.1 to 0.43, better still from 0.17 to 0.25.

A dispersion of invention may comprise from 0.0001% to 50%, preferably 0.1% to 40%, and better still 1% to 25% by weight of oil(s) H1 and H2 relative to the total weight of said composition.

In one embodiment, the fatty phase comprises at least one oil H1, even one oil H2, having a refractive index close to that of the gelling agent(s), to improve the transparency of the fatty phase under consideration and hence the transparency of the dispersion of the invention. In particular, when the fatty phase of a dispersion of the invention also comprises at least one gelling agent selected from among the esters of sugar or polysaccharide and fatty acid(s), in particular of dextrin and fatty acid(s), and most particularly selected from the group formed by dextrin palmitates, dextrin myristates, dextrin palmitates/ethylhexanoates, and mixtures thereof, oil H1 and optionally oil H2 have a refractive index close to that of the gelling agent(s), namely an oil having a refractive index at ambient temperature (25° C.) and atmospheric pressure of between 1.2 and 1.8, preferably between 1.3 and 1.7, in particular between 1.4 and 1.6, and better still between 1.45 and 1.55.

Advantageously, oil H1 having a refractive index between 1.2 and 1.8 is Meadowfoam oil.

Advantageously, oil H2 having a refractive index of between 1.2 and 1.8 is a silicone oil, in particular a phenyl silicone oil e.g. diphenylsiloxyphenyltrimethicone oil such as KF-56 A by Shin Etsu (INCI Name: Diphenylsiloxy Phenyl Trimethicone). Said H2 oil can also be LexFeel® Shine oil by INOLEX (INCI Name: Propylene Glycol Dibenzoate).

Additional Compound(s)

In the invention, the continuous aqueous phase and/or dispersed fatty phase may also comprise at least one additional compound differing from the above-mentioned anionic and cationic polymers, gelling agent and oils.

The dispersions of the invention can also comprise powders; glitter; colouring agents selected in particular from among organic or inorganic colouring agents whether or not water-soluble or liposoluble, materials with optical effect, liquid crystals and mixtures thereof; particulate agents insoluble in the fatty phase; preserving agents; humectants; stabilizers; chelating agents; emollients; modifying agents selected from among texturizing agents, viscosity agents (e.g. aqueous phase gelling/texturizing agents differing from the above-mentioned base), pH modifiers, osmotic strength and/or refractive index modifiers etc. . . . or any usual cosmetic additive; and mixtures thereof.

In one embodiment, the particulate agents insoluble in the fatty phase of the drops are selected from the group formed by pigments, ceramics, polymers in particular acrylic polymers, and mixtures thereof.

The dispersions of the invention can further comprise at least one biological/cosmetic active substance selected from among hydrating agents, healing agents, depigmenting agents, UV filters, peeling agents, antioxidants, active substances stimulating synthesis of dermal and/or epidermal macromolecules, dermo-relaxants, antiperspirant agents, soothing agents and/or anti-ageing agents, and mixtures thereof.

In one embodiment, the dispersion of the invention comprises from 0.00020% to 10%, preferably 0.00025% to 5%, and more preferably 0.0026% to 1% by weight of colouring agent(s) and particularly colourant(s) relative to the total weight of said dispersion.

Among preserving agents particular mention can be made of phenoxyethanol, pentylene glycol and EDTA.

In one embodiment, the dispersions of the invention comprise at least one preserving agent and preferably a mixture of several preserving agents.

Preferably, the weight content of preserving agent(s) is from 0.01% to 10%, preferably 0.5% to 5% by weight relative to the total weight of said dispersion.

In the invention, a dispersion of the invention and in particular the core of the drops (i.e. the fatty phase), may also comprise at least one fragrance in particular such as defined in WO2016096995.

The dispersion of the invention can comprise from 0.01% to 30% by weight of fragrance(s), preferably 0.5% to 20% by weight relative to the total weight of the dispersion.

In one embodiment, the dispersions of the invention may also comprise glycerine. Preferably, a dispersion of the invention may comprise at least 5 weight % of glycerine relative to the total weight of said dispersion.

In addition to texture, the dispersions of the invention afford another advantage compared with «conventional» emulsions since they allow the use of glycerine and furthermore in high content.

In particular, they can comprise glycerine in a content higher than or equal to 10%, higher than or equal to 20%, higher than or equal to 30%, higher than or equal to 40%, even up to 50% by weight relative to the total weight of said dispersion.

In one embodiment, the dispersion of the invention further comprises at least one filler.

A dispersion of the invention can also comprise at least one filler of organic or mineral type, allowing the imparting of additional properties thereto of improved stability with regard to exudation and non-migration properties after application and/or matt finish and/or coverage. By «filler», it is to be understood solid, colourless or white particles of any shape in insoluble form and dispersed in the medium of the composition. Of mineral or organic type, they can impart body or rigidity and/or softness, uniformity of deposit in particular with respect to make-up. The fillers used in the dispersions of the invention can be of lamellar, globular, spherical shape, in the form of fibres or any other intermediate form between these defined shapes. The fillers of the invention may or may not be surface coated, and in particular they can be surface treated with silicones, amino acids, fluorinated derivatives or any other substance promoting the dispersion and compatibility of the filler in the dispersion. Among the fillers able to be used in the invention mention can be made of talc, mica, kaolin, Bentone, precipitated calcium carbonate, magnesium carbonate and hydrogen carbonate, hydroxyapatite, boron nitride, glass or ceramic microcapsules, composites of silica and titanium dioxide such as the TSG series marketed by Nippon Sheet Glass, polyamide powders (Nylon Orgasol by Atochem), poly-b-alanine and polyethylene, polytetrafluoroethylene powders (Teflon), lauroyl lysine, starch, hollow polymer microspheres such as EXPANCEL (NOBEL INDUSTRIE) or Polytrap® (Dow Corning), particles of elastomer polyorganosiloxanes, metal soaps derived from organic carboxylic acids having 8 to 22 carbon atoms, preferably 12 to 18 carbon atoms e.g. zinc, magnesium or lithium stearate, zinc laurate, magnesium myristate, Polypore L 200 (Chemdal Corporation), microbeads of silicone resin (e.g. Tospearl by Toshiba), polyurethane powders in particular crosslinked polyurethane powders comprising a copolymer, said copolymer comprising trimethylol hexyllactone. In particular, it may be a polymer of hexamethylene diisocyanate/trimethylol hexyllactone. Said particles are commercially available e.g. under the trade name PLASTIC POWDER D-400 or PLASTIC POWDER D-800 by TOSHIKI, and mixtures thereof.

The choice of fillers, for obvious reasons, must take into account the process used (in particular of «non-microfluidic» or «microfluidic» type) to produce the dispersion of the invention. This choice lies within the general knowledge of skilled persons.

Texturizing Agent(s)

Depending on the fluidity of the dispersion it is desired to obtain, it is possible to incorporate in the dispersion of the invention one or more texturizing agents differing from the cationic and anionic polymers, gelling agent, oils and fillers described previously.

Evidently, skilled persons will take care to choose any texturizing agent(s) and/or the amount thereof in such manner that the advantageous properties of the dispersion of the invention are not or not substantially affected by the envisaged addition. Also, skilled persons will take care to choose the type and/or amount of texturizing agent(s) as a function of the aqueous or fatty nature of the phase under consideration in the dispersion of the invention.

For example, in a dispersion of the invention, the aqueous phase may comprise at least one texturizing agent differing from the anionic polymer and cationic polymer.

As hydrophilic texturizing agents i.e. soluble or dispersible in water and therefore able to be contained in the aqueous phase of a composition of the invention, the following can be cited:

natural texturizing agents selected in particular from among algae extracts, plant exudates, seed extracts, microorganism exudates e.g. alcasealan (INCI: Alcaligenes Polysaccharides), and other natural agents in particular hyaluronic acid, semi-synthetic texturizing agents selected in particular from among cellulose derivatives and modified starches, synthetic texturizing agents selected in particular from among homopolymers of (meth)acrylic acid or one of the esters thereof, copolymers of (meth)acrylic acid or one of the esters thereof, copolymers of AMPS (2-acrylamido-2-methylpropane sulfonic acid), associative polymers, other texturizing agents selected from among polyethylene glycols (marketed under the trade name Carbowax), clays, silicas such as those marketed under the trade names Aerosil® 90/130/150/200/300/380), glycerine, and mixtures thereof.

By «associative polymer» in the meaning of the invention it is meant any amphiphilic polymer having in its structure at least one fatty chain and at least one hydrophilic portion; associative polymers conforming to the present invention can be anionic, cationic, non-ionic or amphoteric; in particular they can be those described in FR 2 999 921. Preferably, they are the amphiphilic and anionic associative polymers and the amphiphilic and non-ionic associative polymers described below.

These hydrophilic texturizing agents are described in more detail in FR3041251.

Skilled persons will evidently take care to choose any additional compound(s) and/or the amount thereof so that the advantageous properties of the dispersion of the invention are not or not substantially affected by the envisaged addition. In particular, the type and/or amount of the additional compound(s) will depend on the aqueous or fatty nature of the phase under consideration in the dispersion of the invention. These adjustments lie within the competency of skilled persons.

Preparation Method

The dispersions of the invention can be prepared using different methods.

Therefore, the dispersions of the invention have the advantage of being able to be prepared with a simple «non-microfluidic» method, namely by mere emulsification.

As with conventional emulsions, an aqueous solution and a fatty solution are prepared separately. It is the addition under agitation of the fatty phase to the aqueous phase which creates the direct emulsion.

The viscosity of the aqueous phase can be controlled in particular by acting on the amount of anionic polymer (carbomer in particular) and the pH of the solution. In general, the pH of the aqueous phase is lower than 4.5 which can entail the addition of a third sodium hydroxide solution (BF) at a last stage to reach a pH of between 5.5 and 6.5.

The viscosity of the aqueous phase and the shear force applied to the mixture are the two chief parameters which impact the size and monodispersity of the emulsion.

Skilled persons are able to adjust the non-microfluidic method to meet the mean diameter criterion of the dispersion of the invention.

The emulsions of the invention can also be prepared using a microfluidic method, in particular such as described in international applications WO2012/120043 or WO2015/055748.

In this embodiment, the drops obtained with this microfluidic method exhibit uniform size distribution.

Preferably, the dispersions of the invention are composed of a population of monodisperse drops in particular such that they have a mean diameter $\overline{D}$ of 100 µm to 3 000 µm, in particular from 500 µm to 3 000 µm and a coefficient of variation Cv lower than 10%, even lower than 3%.

In the present description, by "monodisperse drops" it is meant the fact that the drop population of the dispersion of the invention has uniform size distribution. Monodisperse drops exhibit good monodispersity. Conversely, drops having poor monodispersity are said to be "polydisperse".

In one embodiment, the mean diameter $\overline{D}$ of the drops is measured for example by analysing a photograph of a batch composed of N drops, using image processing software (Image J). Typically, with this method the diameter is measured in pixels subsequently converted to µm as a function of the size of the container containing the drops of the dispersion.

Preferably, the value of N is chosen to be higher than or equal to 30 so that this analysis reflects the distribution of the drop diameters of said emulsion in a manner that is statistically significant. N is advantageously higher than or equal to 100, especially if the dispersion is polydisperse.

The diameter Di of each drop is measured, and the mean diameter $\overline{D}$ is obtained by calculating the arithmetic mean of these values:

$$\overline{D} = \frac{1}{N}\sum_{i=1}^{N} D_i$$

From these values $D_i$, it is also possible to obtain the standard deviation σ of the diameters of the drops in the dispersion:

$$\sigma = \sqrt{\frac{\sum_{i=1}^{N}(D_i - \overline{D})^2}{N}}$$

The standard deviation σ of a dispersion reflects the distribution of the diameters $D_i$ of the drops of the dispersion around the mean diameter $\overline{D}$.

With knowledge of the mean diameter $\overline{D}$ and standard deviation σ of a dispersion, it is possible to determine that 95.4% of the drop population is found in the diameter range [$\overline{D}-2\sigma$; $\overline{D}+2\sigma$] and that 68.2% of the population is found in the range [$\overline{D}-\sigma$; $\overline{D}+\sigma$].

To characterize the monodispersity of the dispersion in this embodiment of the invention, the coefficient of variation can be calculated:

$$C_v = \frac{\sigma}{D}$$

This parameter reflects the distribution of drop diameters as a function of the mean diameter thereof.

The coefficient of variation Cv of the diameters of the drops in this embodiment of the invention is lower than 10%, preferably lower than 5%, even lower than 3%.

Alternatively, monodispersity can be evidenced by placing a sample of dispersion in a bottle of constant circular cross-section. The bottle is gently agitated by rotating it a quarter of a turn within a half-second about the axis of symmetry passing through the bottle, and it is then left to stand for a half-second before performing similar rotation of the bottle in opposite direction; this operation is repeated four times.

The drops of the dispersed phase organize themselves in crystalline form if they are monodisperse drops. They are therefore stacked in a pattern that is repeated in the three dimensions. It is then possible to observe regular stacking which indicates good monodispersity, irregular stacking translating polydispersity of the dispersion.

To obtain monodisperse drops, it is also possible to use the microfluidic technique (Utada et al. MRS Bulletin 32, 702-708 (2007); Cramer et al. Chem. Eng. Sci. 59, 15, 3045-3058 (2004)), and more particularly microfluidic devices of co-flow type (the fluids flow in the same direction) or flow-focusing type (the fluids flow in different directions and typically in opposite direction).

The presence in the fatty phase of gelling agent(s) may necessitate adjustments to the method for preparing a dispersion of the invention. In particular, the method for preparing said emulsion of the invention may comprise a heating step (between 40° C. and 150° C., in particular between 50° C. and 90° C.) at least of the fatty phase before mixing/contacting said fatty phase with the aqueous phase, and when applicable in the event of a «non-microfluidic» method such as mentioned above, maintaining this heating when agitation is applied until the desired dispersion is obtained.

In one embodiment, the method for preparing dispersions of the invention comprises a step to form the drops, comprising:
  contacting an aqueous fluid FE with an oily fluid FI such as defined below; and
  forming drops of fatty phase composed of the oily fluid FI, dispersed in a continuous aqueous phase composed of fluid FE, said drops optionally comprising a shell isolating the core of the fatty phase drops of the dispersion.

In one embodiment, fluid FI is initially prepared by mixing a fatty phase intended to form the core of drops, at least one gelling agent and at least one oil H1, and optionally in addition at least one first precursor polymer of coacervation e.g. a cationic polymer such as defined above, at least one oil H2 and/or at least one additional compound such as mentioned above.

In one embodiment, the fluid FE is initially prepared by mixing an aqueous phase intended to form the continuous phase of the dispersion, optionally with at least one base, at least one second precursor polymer of coacervation e.g. an anionic polymer such as previously defined, at least one additional compound, preserving agents and/or other water-soluble products such as glycerine.

In one embodiment, the cationic polymer optionally contained in said oily fluid F1 is particularly used to form the shell of the drops.

In one embodiment, the continuous aqueous phase of the formed dispersion comprises and is even composed of the aqueous phase of fluid FE. The anionic polymer optionally contained in said fluid FE is particularly used to form the shell of the drops. Said anionic polymer also contributes towards increasing the viscosity of fluid FE and hence of the continuous aqueous phase.

In one embodiment, the step to form the drops may further comprise a step to inject a solution increasing the viscosity of the continuous aqueous phase of fluid FE. Preferably, the viscosity-increasing solution is aqueous. This viscosity-increasing solution is typically injected into the outer aqueous fluid FE after formation of the dispersion of the invention and therefore after formation of the drops.

In one embodiment, the viscosity-increasing solution comprises a base, in particular an alkali hydroxide such as sodium hydroxide.

In one embodiment, the method for preparing a dispersion of the invention comprises a step to heat the oily fluid F1 comprising the fatty phase of the dispersion, to a temperature of between 40° C. and 150° C., preferably from 50° C. to 90° C., prior to the aforementioned step to form the drops, and therefore before mixing/contacting said fatty phase with the aqueous phase. If a «non-microfluidic» method is used such as mentioned above, this heating step can be maintained throughout the agitation allowing the desired dispersion to be obtained.

In one embodiment, the temperature at the heating step is from 50° C. to 80° C., preferably from 50° C. to 70° C., and more preferably from 55 to 65° C.

In one embodiment, when the oily fluid F1 comprises from 5% to 15% by weight of gelling agent(s) relative to the total weight of said oily fluid FI, said oily fluid FI is advantageously heated to a temperature of 65 to 70° C.

In one embodiment, when the oily fluid F1 comprises from 15% to 99%, preferably 15% to 40% by weight of gelling agent(s) relative to the total weight of said oily fluid FI, said oily fluid FI is heated to a temperature of 80 to 90° C.

In this embodiment, the method for preparing dispersions of the invention comprises the following steps:
  optionally, heating the oily fluid F1 such as described above, even the aqueous fluid FE, to a temperature of between 40° C. and 150° C., preferably from 50° C. to 90° C.;
  contacting the aqueous fluid FE such as described above with the oily fluid FI; and
  forming the drops of the fatty phase, composed of the oily fluid FI, dispersed in a continuous aqueous phase composed of fluid FE, said drops optionally comprising a shell isolating the core of fatty phase drops of the dispersion,
  where:
  the oily fluid FI comprises at least one gelling agent and at least one oil H1, and optionally at least one cationic polymer such as previously defined, amodimethicone in particular, at least one oil H2 and/or at least one additional compound such as mentioned above; and
  the aqueous fluid FE at least comprises water, and optionally at least one anionic polymer such as previously defined, in particular a carbomer, at least one additional compound such as mentioned above.

Uses

Preferably, the dispersion of the invention can be used directly, after the aforementioned preparation methods, as composition particularly a cosmetic composition. The dispersion of the invention, when prepared with a microfluidic method such as described above, can also be used as composition particularly a cosmetic composition after separation of the drops and redispersion thereof in a second suitable phase.

The invention also concerns the use of a dispersion of the invention to prepare a composition particularly a cosmetic composition.

The present invention also concerns a composition particularly a cosmetic composition comprising at least one dispersion of the invention in association with a physiologically acceptable medium.

The dispersions or compositions of the invention can notably be used in the cosmetic field.

In addition to the above-mentioned ingredients, they may also comprise at least one physiologically acceptable medium.

In the invention, and unless otherwise stated, by "physiologically acceptable medium" it is meant a medium appropriate for cosmetic applications, and suitable in particular for application of a composition of the invention onto keratin material, particularly the skin and/or hair and more particularly the skin.

The physiologically acceptable medium is generally adapted to the type of medium onto which the composition is to be applied and to the appearance under which the composition is to be packaged.

In one embodiment, the physiologically acceptable medium is directly represented by the continuous aqueous phase such as described above.

For example, the cosmetic compositions of the invention can be a cream, emulsion, lotion, serum, gel and oil for the skin (hands, face, feet, etc.), a foundation (liquid, paste), a bath and shower preparation (salts, foams, oils, gels, etc.), a hair care product (hair dyes and bleaches), a cleansing product (lotions, powders, shampoos), a hair treatment product (lotions, creams, oils), a hair styling product (lotions, lacquers, brilliantine), a shaving product (soaps, foams, lotions, etc.), a product intended to be applied to the lips, a sun product, self-tanning product, skin lightening product, an antiwrinkle product. In particular the cosmetic compositions of the invention can be an anti-ageing serum, a youth serum, a hydrating serum or scented water.

The present invention also concerns a non-therapeutic method for cosmetic treatment of keratin material, in particular the skin and/or hair and more particularly the skin, comprising a step to apply to said keratin material at least one dispersion or at least one layer of an above-mentioned cosmetic composition.

The present invention also concerns the use of at least one non-volatile hydrocarbon oil H1 containing more than 90%, preferably more than 95% of fatty acids having at least 18 carbon atoms, preferably at least 20 carbon atoms such as defined previously, to improve the transparency of a dispersion of the invention and in particular to reduce and even prevent:
- the opacification phenomenon of the continuous aqueous phase,
- the leakage of material particularly of oil(s) and/or gelling agent(s) from the dispersed phase towards the continuous aqueous phase,
- the adhesion of drops onto the walls of packaging, and/or the drop aggregation, and therefore:
- to maintain, even improve, the stability over time and the visual impact of said dispersion of the invention.

Throughout the entire description, the expression «comprising one» is to be construed as being a synonym of «comprising at least one», unless otherwise specified.

The expressions «between . . . and . . .», «from . . . to . . .» and «ranging from . . . to . . .» are to be understood to include the limits, unless otherwise specified.

The quantities of ingredients given in the examples are expressed as weight percentages relative to the total weight of the composition, unless stated otherwise.

The following examples illustrate the present invention without limiting the scope thereof.

EXAMPLES

Unless otherwise stated, the dispersions described below result from a microfluidic method, in particular such as described above or in WO2017046305. The microfluidic system used is composed of two parts, a first part in which contacting under heat (between 75 and 90° C.) is carried out between IF (or FI) and OF (or FE) to form a dispersion, and a second part ensuring rapid cooling of the dispersion thus formed to accelerate gelling kinetics and thereby prevent post-formation risks of coalescence of the drops (cooling temperature: between 5 and 28° C.).

Example 1: Preparation of Dispersions of Macroscopic Drops with or without Non-Volatile Hydrocarbon Oil of the Invention In this example, dispersions of macroscopic drops were prepared of a gelled fatty phase dispersed in a continuous aqueous phase. The compositions of the phases (fluids) allowing the preparation of the dispersions were as follows:

| Fluid | Name | INCI | 1A (comp.) % w/w | 1B (comp.) % w/w | 1C (inv.) % w/w | 2A (comp.) % w/w | 2B (comp.) % w/w | 2C (inv.) % w/w |
|---|---|---|---|---|---|---|---|---|
| IF (gelled fattyphase) | DUB ININ Grade A | Isononyl isononanoate | | | QSP* | | | |
| | Argan oil | *Argania spinosa* kernel oil | 0 | 18.00 | 0 | 0 | 18.00 | 0 |
| | Meadowfoam oil | *Limnanthes alba* seed oil | 0 | 0 | 18.00 | 0 | 0 | 18.00 |
| | Rheopearl KL2 | Dextrin palmitate, Palmitic Acid, Aqua | | | | 20.00 | | |

-continued

| Fluid | Name | INCI | 1A (comp.) % w/w | 1B (comp.) % w/w | 1C (inv.) % w/w | 2A (comp.) % w/w | 2B (comp.) % w/w | 2C (inv.) % w/w |
|---|---|---|---|---|---|---|---|---|
| | PHAT BLUE DC6204 | CI 61565 (and) CI 60725 | | | 0.00092 | | | |
| | CAS-3131 PILOT | Amodimethicone | | 0 | | | 0.15 | |
| | | Total | | | 100 | | | |
| OF (continuous aqueous phase) | Reverse osmosis water | Aqua | | | Q.S. | | | |
| | Microcare PE | Phenoxyethanol, aqua | | | 0.89 | | | |
| | Microcare emollient PTG | Pentylene glycol, aqua | | | 2.22 | | | |
| | Glycerine codex | Glycerin, aqua | | | 11.11 | | | |
| | Edeta BD | Disodium EDTA | | | 0.044 | | | |
| | Carbopol ETD 2050 polymer | Carbomer | | | 0.33 | | | |
| | Sodium hydroxide pellets PRS codex | Sodium hydroxide | | | 0.013 | | | |
| | | Total | | | 100 | | | |
| BF (base) | Reverse osmosis water | Aqua | | | Q.S. | | | |
| | Sodium hydroxide pellets PRS codex | Sodium hydroxide | | | 0.35 | | | |
| | | Total | | | 100 | | | |

*Q.S.: as much as is sufficient

Tests 2A-2C differed from tests 1A-1C through the presence of amodimethicone in the gelled fatty phase. This led to the formation of a membrane at the water-oil interface resulting from an interfacial complex coacervation reaction between amodimethicone and the carbomer.

Preparation Protocol:

For OF:

Phenoxyethanol, Pentyleneglycol and EDTA are incorporated in the water. The mixture is stirred for 5 min.

The carbomer is dispersed in the preceding mixture under stirring for 30 minutes using an impeller of disperser blade type.

Glycerine is then added and the mixture left under stirring for 10 min.

Sodium hydroxide is added and the solution is mixed for 10 minutes.

For IF:

Amodimethicone, if used (i.e. tests 2A to 2C), is added to isononyl isononanoate and stirred with a magnetic stir bar for 5 min. PHAT BLUE DC6204 colouring agent is added under stirring.

Under stirring, argan oil and Meadowfoam oil are added.

The mixture is heated to 80° C., after which Rheopearl KL2 is added under magnetic stirring until a homogeneous solution is obtained.

The heated IF solution is placed in a syringe connected to heating to maintain the heat of IF (80° C.). To reduce heat losses, the microfluidic device is positioned directly at the outlet of the syringe.

For BF: sodium hydroxide and water are mixed with a magnetic stir bar for 5 min.

In these tests, the following flow rates were used:

| OF | 150 mL/hr |
|---|---|
| IF | 20.35 mL/hr |
| BF | 16.667 mL/hr |

The dispersions obtained comprised drops having a mean diameter larger than 100 μm, in particular larger than 300 μm.

Parameters Analysed:

After production, each test sample of Example 1 was packaged in three 30 ml polypropylene containers filled to one half. After 1 day at ambient temperature, each test sample was subjected to one of the three following transport tests (one container per test), namely:

roller test (i.e. horizontal circular movement): reference Wheaton, for 1 hour;

vibrating table (i.e. vertical circular movement): reference Heidolph Unimax 1010, for 1 hour; and 3D mixer (i.e. random movements): for 6 minutes.

On completion of these 3 tests, the parameters of adhesion, aggregation and turbidity (or opacification) of the continuous aqueous phase were analysed (visual observation).

| ADHESION | AGGREGATION | TURBIDITY |
|---|---|---|
| Attachment of drops to the wall of packaging | Drops aggregating together (aggregation is likely to promote coalescence) | Transfer of the fatty phase into the continuous aqueous phase |

Score Criteria:

| SCORE CRITERIA | 0 | 1 | 2 | 3 |
|---|---|---|---|---|
| ADHESION | No adhesion | Slight adhesion | Moderate adhesion | Strong adhesion |
| AGGREGATION | No aggregation | Slight aggregation | Moderate aggregation | Strong aggregation |
| GEL TURBIDITY | Transparent gel | Slightly turbid gel | Moderately turbid gel | Turbid gel |

Results:

|  | 1A (comp.) | 1B (comp.) | 1C (invention) | 2A (comp.) | 2B (comp.) | 2C (invention) |
|---|---|---|---|---|---|---|
| ADHESION | 3 | 3 | 2 | 2 | 2 | 1 |
| AGGREGATION | 2 | 2 | 1 | 2 | 2 | 0 |
| GEL TURBIDITY | 2 | 2 | 0 | 1 | 1 | 0 |

The above tests were reproduced by replacing, for tests 1c and 2C, Meadowfoam oil by jojoba oil (same % s). The results obtained were slightly lower than with Meadowfoam oil but nevertheless distinctly more satisfactory than with argan oil.

Within the context of a dispersion formed of macroscopic drops of gelled fatty phase in a continuous aqueous phase, the use of at least one non-volatile hydrocarbon oil of the invention therefore efficiently reduces the phenomenon of opacification of the continuous aqueous phase but also reduces drop aggregation (and hence risks of coalescence) as well as adhesion of drops onto packaging walls.

It is also observed that the presence of a membrane (i.e. 2A-2C) reinforces these advantages in terms of reducing the opacification phenomenon of the continuous aqueous phase, reducing drop adhesion onto packaging walls, and even reducing drop aggregation.

This contributes towards maintaining the unique, distinguishing visual impact of said dispersions.

Example 2: Impact of the Content of Non-Volatile Hydrocarbon Oil in the Invention In this example, dispersions of macroscopic drops of a gelled fatty phase were prepared dispersed in a continuous aqueous phase. The compositions of the phases (fluids) allowing the preparation of the dispersions were the following:

| Fluid | Nom | INCI | 3A (comp.) % w/w | 3C (inv.) % w/w | 3D (inv.) % w/w |
|---|---|---|---|---|---|
| IF (gelled fatty phase) | DUB ININ Grade A | Isononyl isononanoate | | Q.S. | |
| | Meadowfoam oil | Limnanthes alba seed oil | 0 | 18.00 | 30.00 |
| | Rheopearl KL2 | Dextrin palmitate, Palmitic Acid, Aqua | | 15.00 | |
| | PHAT BLUE DC6204 | CI 61565 (and) CI 60725 | | 0.00092 | |
| | CAS-3131 PILOT | Amodimethicone | | 0.15 | |
| | | Total | | 100 | |
| OF (continuous aqueous phase) | Reverse osmosis water | Aqua | | Q.S. | |
| | Microcare PE | Phenoxyethanol, aqua | | 0.89 | |
| | Microcare emollient PTG | Pentylene glycol, aqua | | 2.22 | |
| | Glycerine codex | Glycerin, aqua | | 15.00 | |
| | Zemea propanediol | Propanediol, aqua | | 4.80 | |
| | Butylene glycol 1.3 | Butylene glycol, aqua | | 5.30 | |
| | Edeta BD | Disodium EDTA | | 0.044 | |
| | Carbopol ETD 2050 polymer | Carbomer | | 0.33 | |
| | Sodium hydroxide pellets PRS codex | Sodium hydroxide | | 0.013 | |
| | | Total | | 100 | |

-continued

| Fluid | Nom | INCI | 3A (comp.) % w/w | 3C (inv.) % w/w | 3D (inv.) % w/w |
|---|---|---|---|---|---|
| BF (base) | Reverse osmosis water | Aqua | | Q.S. | |
| | Sodium hydroxide pellets PRS codex | Sodium hydroxide | | 0.35 | |
| | | Total | | 100 | |

The preparation protocol, analysed parameters and score criteria were the same as those described in Example 1.

The dispersions obtained comprise drops having a mean diameter larger than 100 μm, in particular larger than 300 μm.

Results:

| | 3A (comparative) | 3C (invention) | 3D (invention) |
|---|---|---|---|
| ADHESION | 2 | 1 | 1 |
| AGGREGATION | 2 | 1 | 1 |
| GEL TURBIDITY | 1 | 0 | 0 |

An increase in the content of Meadowfoam oil (i.e. 3C vs 3D) does not have any impact on the opacification phenomenon of the continuous aqueous phase, on drop aggregation (and hence risks of coalescence) or on drop adhesion to packaging walls.

However, an increase in the content of gelling agent in the dispersed fatty phase (i.e. 2C vs 3C) allows a further reduction in drop aggregation and hence in risks of coalescence.

The invention claimed is:

1. A dispersion containing a dispersed phase comprising drops and a continuous aqueous phase, wherein the drops comprise a fatty phase containing at least one gelling agent, and wherein the fatty phase comprises at least one non-volatile hydrocarbon oil H1 containing more than 90% of fatty acids having at least 20 carbon atoms, wherein oil H1 comprises more than 90% of fatty acids selected from the group consisting of: eicosenoic acid, docosanoic acid, docosadienoic acid, and mixtures thereof.

2. The dispersion of claim 1, wherein at least 60% of the drops have a mean diameter larger than or equal to 100 μm.

3. The dispersion of claim 1, wherein the drops having a diameter larger than or equal to 100 μm represent a volume greater than or equal to 60% of the total volume of the dispersed phase.

4. The dispersion of claim 1, wherein the drops comprise a shell.

5. The dispersion of claim 1, wherein the fatty phase comprises between 1% and 50% by weight of oil(s) H1 relative to the total weight of said fatty phase.

6. The dispersion of claim 1, wherein oil H1 is selected from among vegetable oils.

7. The dispersion of claim 1, wherein the gelling agent is selected from the group consisting of: organic or mineral, polymeric or molecular lipophilic gelling agents; fats solid at ambient temperature and pressure, and mixtures thereof.

8. The dispersion of claim 1, comprising from 0.5% to 99% by weight of gelling agent(s) relative to the total weight of the fatty phase.

9. The dispersion of claim 1, characterized in that it does not comprise a surfactant.

10. A composition comprising a dispersion of claim 1, in association with a physiologically acceptable medium.

11. The dispersion of claim 1, wherein the drops comprise a shell, said shell comprising at least one anionic polymer and at least one cationic polymer.

12. The dispersion of claim 11, wherein the cationic polymer is a silicone polymer modified by a primary, secondary or tertiary amine function.

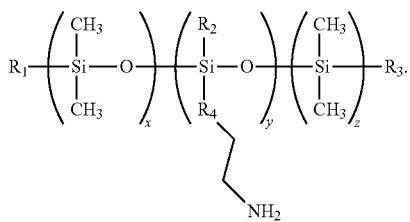

13. The dispersion of claim 11, wherein the anionic polymer is a polymer comprising monomer units including at least one carboxylic acid chemical function.

14. The dispersion of claim 11, wherein the cationic polymer has the following formula:

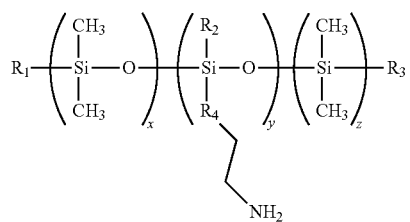

where:

$R_1$, $R_2$ and $R_3$ are each independently OH or $CH_3$;

$R_4$ is a group —$CH_2$— or group —X—NH— where X is a C3 or C4 divalent alkylene radical;

x is an integer of between 10 and 5 000;

y is an integer of between 2 and 1 000; and z is an integer of between 0 and 10.

15. The dispersion of claim 11, wherein the anionic polymer is selected from among carbomers and acrylates/$C_{10-30}$ alkyl acrylate crosslinked copolymers.

16. The composition of claim 1, wherein the non-volatile hydrocarbon oil H1 contains more than 95% of fatty acids having at least 20 carbon atoms.

17. A method for preparing a dispersion of claim 1, comprising the following steps:

optionally, heating an oily fluid FI to a temperature of between 40° C. and 150° C.;

contacting an aqueous fluid FE with the oily fluid FI; and forming drops of fatty phase composed of the oily fluid FI dispersed in a continuous aqueous phase composed of fluid FE, said drops optionally comprising a shell isolating the core of fatty phase drops of the dispersion, wherein:

the oily fluid FI comprises at least one gelling agent and at least one non-volatile hydrocarbon oil H1 containing more than 90% of fatty acids having at least 20 carbon atoms and optionally at least one cationic polymer, and the aqueous fluid FE at least comprises water and optionally at least one anionic polymer.

18. A non-therapeutic method for the cosmetic treatment of keratin material, comprising a step of applying to said keratin material a dispersion of claim 1.

19. A method to (i) improve the transparency of a dispersion of claim 1 by reducing or preventing:

the opacification phenomenon of the continuous aqueous phase, the leakage of material from the dispersed phase towards the continuous aqueous phase, the drop adhesion onto the walls of packaging, and/or the drop aggregation, and (ii) to maintain or improve the stability over time and the visual impact of said dispersion, said method involving the use of at least one non-volatile hydrocarbon oil H1 containing more than 90% of fatty acids having at least 20 carbon atoms.

20. The method of claim 19, wherein the material comprises oil(s) and/or gelling agent(s).

21. A non-therapeutic method for the cosmetic treatment of keratin material, comprising a step of applying to said keratin material at least one layer of a cosmetic composition of claim 10.

* * * * *